United States Patent [19]

Sebille et al.

[11] Patent Number: 4,694,015
[45] Date of Patent: Sep. 15, 1987

[54] PHARMACEUTICAL OR VETERINARY COMPOSITIONS CONTAINING THIOSULFONATE DERIVATIVES

[75] Inventors: Bernard Sebille, Clamart; Yves Beuzard, Paris; Henri Demarne, Montpellier, all of France

[73] Assignees: Sanofi; Institut National de la Sante et de la Recherche Medicale (Inserm), both of Paris, France

[21] Appl. No.: 797,486

[22] Filed: Nov. 13, 1985

[30] Foreign Application Priority Data

Nov. 13, 1984 [FR] France ................................. 84 17286

[51] Int. Cl.$^4$ .................... A61K 31/42; A61K 31/415
[52] U.S. Cl. ................................... 514/375; 514/395; 514/397; 514/398
[58] Field of Search ................ 514/375, 395, 397, 398

[56] References Cited

PUBLICATIONS

C.A., vol. 82, No. 17, p. 507, 111998u.
C.A., vol. 71, No. 11, p. 383, 49830a.
C.A., vol. 92, No. 3, p. 677, 22420p.
C.A., vol. 96, No. 14, p. 637, 113510s.
Chemical Abstracts 99:222446h (1983).
Chemical Abstracts 96:113510s (1982).

Primary Examiner—Jerome D. Goldberg
Attorney, Agent, or Firm—Bacon & Thomas

[57] ABSTRACT

The invention relates to pharmaceutical or veterinary compositions for inhibiting the malformation or destruction of red blood corpuscules due to a genetic modification of haemoglobin or to parasites, compositions comprising, as active ingredient, at least one thiosulfonate derivative of general formula:

$$R-S-SO_2-R_1$$

in which R represents a 1-methyl-imidazol-2-yl, 1H-benzimidazol-2-yl or benzoxazol-2-yl radical and $R_1$ represents a lower alkyl, (hydroxy) lower alkyl, lower alkanoyl, phenyl, (lower alkyl) phenyl, (hydroxy lower alkyl) phenyl, (lower alkanoyl) phenyl or quinolin-8-yl radical.

The compositions in question can be used in the treatment of drepanocytosis, malaria and babebiosis.

16 Claims, No Drawings

PHARMACEUTICAL OR VETERINARY COMPOSITIONS CONTAINING THIOSULFONATE DERIVATIVES

The present invention relates to pharmaceutical or veterinary compositions for inhibiting the malformation or destruction of red blood corpuscules due to a genetic modification of haemoglobin or to parasites.

More particularly, the invention concerns pharmaceutical or veterinary compositions containing, as essential active ingredient, at least one thiosulfonate derivative of general formula:

$$R-S-SO_2-R_1 \qquad I$$

in which R represents a 1-methyl-imidazol-2-yl, 1H-benzimidazol-2-yl or benzoxazol-2-yl radical and $R_1$ represents a lower alkyl, (hydroxy)lower alkyl, lower alkanoyl, phenyl, (lower alkyl)phenyl, (hydroxy lower alkyl)phenyl, (lower alkanoyl)phenyl or quinolin-8-yl radical.

Likewise, the invention relates to a method for inhibiting the malformation or destruction of red blood corpuscules due to a genetic modification of the haemoglobin or to parasites in a host in need of such inhibitory treatment whereby an effective dose of at least one thiosulfonate derivative of the invention is administered to the said host.

As used herein, the term "lower alkyl" means more particularly the methyl, ethyl, n-propyl and isopropyl groups and the term "lower alkanoyl" designates more particularly the formyl, acetyl and propionyl groups.

Drepanocytosis is known to be a genetic diseases involving an abnormality in the structure of the haemoglobin, whereby the Glu-6 amino acid of the β-chain is replaced by Val amino acid, giving haemoglobin-S which polymerizes.

The polymerization, during deoxygenation of the red cells, brings about sickling of the latter which become rigid, circulate poorly and are blocked in the small vessels. Individuals carrying two sickle cell genes are thus under the permanent threat of a fatal complication.

Certain disulfides have been described in the literature as inhibiting sickling, in particular cystamine, which has been found to be particularly active. ("Developments of Therapeutic Agents for Sickle Cell Disease", Inserm Symposium, 1979, North Holland: Amsterdam, Editors J. ROSA, Y. BEUZARD, J. HERCULES; p. 139-153).

On the other hand, no thiosulfonate derivative is known, at present, as presenting such an inhibitory action against sickling.

It has now been found that thiosulfonate derivatives i.e. the compounds of formula I above exert a marked inhibitory action against the polymerization of the haemoglobin-S and the sickling of the red cells.

It has also been unexpectedly found that the thiosulfonate derivatives of formula I are active against parasites affecting the red blood corpuscules, such as the Plasmodia and the Babesiae.

More particularly, the compounds of formula I have shown a schizonticide action in vitro on *Plasmodium falciparum* and in vivo on *Plasmodium berghei*.

The expression "inhibiting the malformation or destruction of red blood corpuscules" as used in the present context, means an inhibitory action which may be exerted either directly on the haemoglobin or indirectly by inhibition of the growth of parasites in the red cell.

In addition, the level of toxicity of compounds of formula I is not such as the hinder their therapeutic use.

Therefore, the compounds of formula I can be regarded as very valuable agents for inhibiting the malformation or destruction of red blood corpuscules due to a genetic modification of the haemoglobin or to parasites and therefore useful in the treatment of drepanocytosis, malaria and babebiosis.

Inhibition of the sickling of human red blood corpuscules was assessed by washing and incubating, in a saline buffer (pH: 7.40; 0.15M) for one hour at 37° C., the red cells of subjects suffering from drepanocytosis. This operation was carried out in a water-bath under stirring and in the presence of a compound of formula I used at different concentrations. The molar ratios between the compound of formula I and the haemoglobin were initially tested at intervals ranging from 0.5 to 20, the mM concentration in haemoglobin being 0.5 in each case and the ratio being modified according to the results obtained.

At the end of incubation, the excess of the product being tested was removed by washing and the cellular suspension adjusted so as to form a haematocrit of 5% was transferred to an Erlenmeyer flask and incubated at 37° C. under a current comprising a humidified mixture of nitrogen and oxygen the oxygen concentration being regulated by a gas-mixing pump. The effluent gas was then transferred to another tube containing formaldehyde and, at the end of incubation, the cellular suspension was transferred to the formaldehyde by merely turning the flask upside down.

The proportion of deformed cells and those having the characteristics of drepanocytes (having two filiform extensions) was assessed with the aid of a microscope having a NORMARSKY interferential optical system. Inhibition of sickling was calculated according to the following formula:

$$\frac{\% \text{ sickle-shaped cells used as controls} - \% \text{ sickle-shaped cells in the presence of the compound of formula I}}{\% \text{ sickle-shaped cells used as controls}}$$

The following results were obtained with a representative compound of formula I in comparison with cystamine. These results represent the percentage of inhibition of sickling of the red blood corpuscules.

| Compound | Concentration (mmolar) | % inhibition |
| --- | --- | --- |
| Benzoxazol-2-yl p-toluene-thiosulfonate | 5 | 100 |
| Cystamine | 5 | 33 |

These results show that the compound of formula I inhibits sickling of the red blood corpuscules of patients suffering from drepanocytosis and are more active than the comparison compound.

The compounds of formula I above are known compounds having been published in Japanese Patent Applications Nos. 81-99335 (C.A. 96, 113510s) and 82-140187 (C.A. 99, 222446g) as photothermographic products without any pharmacological activity or therapeutic use being attributed to them.

These compounds of formula I can be prepared, in particular, by reacting, in the presence of an acid acceptor such as for example pyridine, a mercapto derivative of general formula:

$$R—SH \quad\quad II$$

in which R has the same meaning as above, with a halogenosulfonyl derivative of general formula:

$$Hal—SO_2—R_1 \quad\quad III$$

in which $R_1$ has the same meaning as above and Hal represents a halogen atom, preferably chlorine.

The reaction can be carried out in an appropriate organic solvent such as, for example, dichloromethane or acetonitrile.

The molar ratio between the mercapto derivative of formula II and the halogenosulfonyl derivative of formula III is of paramount importance as is also the temperature, in regard to the yield in thiosulfonate derivative of formula I.

Thus, at room-temperature and following the molar ratio:

$$\frac{\text{compound of formula II}}{\text{compound of formula III}} = 2,$$

it is mainly the disulfides of formula R—S—S—R, in which R has the same meaning as above, which are obtained.

For instance, 90% of 2,2'-dithio-di-1H-benzimidazole is produced at room-temperature from 2-mercapto-1H-benzimidazole and benzenesulfonyl chloride in a 2:1 molar ratio.

However, by controlling the temperature and modifying the molar ratio of the reagents of formulae II and III, it is principally the thiosulfonate derivatives of formula I which are produced.

The process hereabove described is therefore carried out at a temperature from 0° to 10° C., generally at the temperature of iced water, the molar ratio $$\frac{\text{compound of formula II}}{\text{compound of formula III}}$$

varying from 1:1 to 1:4. Generally, a 1:2 molar ratio is preferred.

It will be appreciated that, for therapeutic use, the compounds of formula I will normally be administered as active principle, in the form of a pharmaceutical or veterinary composition which may be in a dosage unit form appropriate to the desired mode of administration, for instance for oral, sublingual, sub-cutaneous, intramuscular, intravenous, transdermic or rectal administration.

Thus, the composition may be in a dosage unit form suitable for oral administration for example a coated or uncoated tablet, a hard- or soft-gelatin capsule, a packaged powder, a suspension or a syrup for oral administration, a suppository for rectal administration, a sterile solution or suspension for parenteral administration.

When in dosage unit form, the composition may contain from 10 to 1000 mg of active principle per dosage unit form intended for oral, rectal or parenteral route.

Generally, one dosage unit will be required 1 to 4 times a day so that the daily dosage of active principle of formula I can vary from 0.1 to 100 mg per kg of body-weight for the treatment of drepanocytosis, malaria and babebiosis.

Irrespective of the form which they may take, the pharmaceutical or veterinary compositions of the invention will normally be prepared by associating at least one of the compounds of formula I with an appropriate pharmaceutical carrier or excipient, for example one or more of the following substances: distilled water, benzyl alcohol, lactose, starches, talc, magnesium stearate, polyvinylpyrrolidone, alginic acid, colloidal silica, microcrystalline cellulose, phthalic or acrylic esters, titanium dioxide, flavouring agents etc . . . .

A more detailed but non limitative description is given hereunder of various methods of preparing the compositions of the invention.

Powders for oral administration may be prepared, for example, by merely crushing the active principle to a suitably fine consistency and mixing it with a diluent similarly treated which may be, for instance, an edible glucide derivative such as starch.

Preferably, a sweetening agent or a sugar together with a flavouring oil will be included.

To obtain a liquid composition for oral administration, granules are prepared by wetting the active principle of formula I and a water-soluble diluent such as saccharose, glucose, etc . . . , with a binding agent such as acacia mucilage, gelatin solution or methylcellulose solution and forcing the resulting product through a screen to form granules which are then dried.

Preferably, the composition will contain a suspension agent such as gum tragacanth.

Similarly, a composition of the invention in the form of a capsule may be obtained by introducing a pulverulent mixture as described above into previously prepared soft- or hard-gelatin shells.

As an aid in the filling operation, it will be advantageous to add a lubricant such as talc, magnesium stearate or calcium stearate to the pulverulent mixture.

Tablets can also be obtained by first preparing a pulverulent mixture from an active compound of formula I suitably crushed and a diluent or a base such as starch, saccharose, kaolin, dicalcium phosphate etc . . . . This pulverulent mixture is then granulated or cut up after a lubricant has been added and is finally compressed.

The pulverulent mixture may be granulated by wetting with a binding agent such as syrup, starch paste or acacia mucilage and forcing it through a screen.

Another method of granulation consists in dividing up the pulverulent mixture, by passing it through a tablet-making apparatus and then fragmenting the imperfectly formed tablets obtained. The fragments may be lubricated by adding a stearate salt, talc or mineral oil to prevent them from forming cubes by sticking to each other.

The lubricated mixture is then compressed to form the final tablets.

The tablets may be covered with a protective coating or an enteric-coating or again coated so that the active principle is gradually released.

A composition of the invention for rectal administration can also be prepared in the form of a suppository by pouring, into an appropriate mould, a mixture formed of the active principle of formula I and a binding agent melting at rectal temperature, for instance cocoa butter, polyethyleneglycols or lanoline.

For parenteral administration, aqueous suspensions, isotonic saline solutions or sterile and injectable solutions can be prepared comprising an active compound of formula I together with a solubilizing agent, if required, for example polysorbate 80, appropriate wetting agents for instance propyleneglycol or butyleneglycol and a preserving agent such benzyl alcohol.

The active principle can also be presented in the form of microcapsules optionally with one or more additives.

The non-limitative Examples which follow illustrate the preparation of compounds of formula I together with compositions containing them.

EXAMPLE 1

Preparation of 1H-benzimidazol-2-yl benzenethiosulfonate

In a 500 ml three necked flask fitted with a condenser and a magnetic stirrer were dissolved, under adequate stirring, 3.51 g (0.02 mol) of benzenesulfonyl chloride in 40 ml of dichloromethane. To the solution so formed, there were added 3.16 g (0.04 mol) of pyridine previously dried on magnesium sulfate.

The flask was placed in a bath of water at 4° C. and while the reaction medium was maintained under stirring at the temperature of the iced water there was slowly added (addition period: >3 hours) drop-by-drop 1.5 g (0.01 mol) of 2-mercapto-1H-benzimidazole dissolved in 160 ml of dichloromethane.

The reaction medium was kept under vigorous stirring for 24 hours at 4° C. A cream-coloured precipitate progressively appeared in the flask. To facilitate the formation and recovery of the solid, a part of the solvent was evaporated off under vacuum by very gentle heating (about 50° C.).

The precipitate was collected by filtration on fritted glass and dried. The product was then washed 3 times with ethanol and recrystallised from the same solvent.

In this manner, 1H-benzimidazole-2-yl benzenethiosulfonate was obtained.

Yield: 80%

Empirical formula: $C_3H_{10}N_2O_2S_2$

Analysis:

|  | C % | H % | N % | O % | S % |
|---|---|---|---|---|---|
| Calculated | 53.78 | 3.47 | 9.65 | 11.02 | 22.08 |
| Found | 53.71 | 3.51 | 10.19 | 11.60 | 21.69 |

M.P.: 201° C.

Following the same procedure as that described above, the following compounds were obtained:

(a) From p-toluenesulfonyl chloride and 2-mercapto-1H-benzimidazole, 1H-benzimidazol-2-yl p-toluenethiosulfonate.

Yield: 70%

Empirical formula: $C_{14}H_{12}N_2O_2S_2$

Analysis:

|  | C % | H % | N % | O % | S % |
|---|---|---|---|---|---|
| Calculated | 55.24 | 3.97 | 9.20 | 10.51 | 21.07 |
| Found | 55.24 | 3.92 | 9.19 | 10.46 | 21.07 |

M.P.: 169° C.

(b) From benzenesulfonyl chloride and 1-methyl-2-mercapto-1H-imidazole, 1-methyl-1H-imidazol-2-yl benzenethiosulfonate.

Yield: 45%

Empirical formula: $C_{10}H_{10}N_2O_2S_2$

Analysis:

|  | C % | H % | N % | O % | S % |
|---|---|---|---|---|---|
| Calculated | 47.23 | 3.96 | 11.01 | 12.58 | 25.21 |
| Found | 46.98 | 4.37 | 11.07 | 12.77 | 24.81 |

M.P.: 84° C.

(c) From p-toluenesulfonyl chloride and 2-mercaptobenzoxazole, benzoxazol-2-yl p-toluenethiosulfonate.

Yield: 75%

Empirical formula: $C_{14}H_{11}NO_3S_2$

Analysis:

|  | C % | H % | N % | O % | S % |
|---|---|---|---|---|---|
| Calculated | 55.07 | 3.63 | 4.59 | 15.72 | 21.00 |
| Found | 54.49 | 3.61 | 5.03 | 15.91 | 20.95 |

M.P.: 93° C.

(d) From methanesulfonyl chloride and 2-mercapto-1H-benzimidazole, 1H-benzimidazole-2-yl methanethiosulfonate.

Yield: 50%

Empirical formula: $C_8H_8N_2O_2S_2$

Analysis:

|  | C % | H % | N % | O % | S % |
|---|---|---|---|---|---|
| Calculated | 42.09 | 3.53 | 12.27 | 14.02 | 28.09 |
| Found | 42.05 | 3.62 | 12.17 | 14.61 | 27.47 |

M.P.: 157° C.

EXAMPLE 2

Tablets were prepared containing, as active ingredient, a thiosulfonate derivative of formula I, associated with a carrier to form the composition given hereunder:

|  | mg |
|---|---|
| Compound of formula I | 500 |
| Glycine | 120 |
| Microcrystalline cellulose | 70 |
| Precipitated silica | 18 |
| Carboxymethylstarch | 30 |
| Magnesium stearate | 11 |
| Talc | 11 |

The ingredients of the above composition were mixed for 30 minutes and the resulting mixture was granulated dry and passed through a sieve with 1.6 mm mesh. The mixture was then compressed using a punch in the form of a small rod. Tablets were thus obtained each weighing 760 mg and each containing 500 mg of active ingredient.

EXAMPLE 3

Coated tablets were prepared by coating the tablets obtained in Example 2 with a suspension of dibutyl phthalate, butyl and dimethylaminoethyl polymethacrylate, polyethyleneglycol 1500, precipitated silica, titanium dioxide and talc in a 1:1 acetone/isopropanol mixture having a concentration of dry residue of about 10%.

In this manner, coated tablets were obtained each weighing 780 mg and each containing 500 mg of active ingredient.

EXAMPLE 4

Granules intended for the reconstitution of a liquid preparation for oral adminsitration were prepared containing, as active ingredient, a thiosulfonate derivative of formula I, associated with a carrier to form the following composition:

|  | g |
|---|---|
| Compound of formula I | 3.60 |
| Saccharose | 50.00 |
| Sodium carboxymethylcellulose | 0.80 |
| Citric acid | 0.10 |
| Trisodium citrate | 0.90 |
| Sodium benzoate | 0.25 |
| Sodium saccharine | 0.15 |
| Flavouring agent | 0.50 |

The above ingredients, with the exception of saccharose, were pulverized and the powder so obtained was mixed with the saccharose until homogeneous granules were obtained.

The volume of the granules so provided was increased to 100 ml with water intended for the preparation of syrups.

A unit dose of 5 ml of the extemporaneous syrup thus obtained contained 180 mg of active principle.

EXAMPLE 5

Granules intended for the reconstitution of an oral liquid preparation having the composition given below were prepared as described in Example 4:

|  | g |
|---|---|
| Compound of formula I. | 7.00 |
| Saccharose | 46.60 |
| Sodium carboxymethylcellulose | 0.90 |
| Citric acid | 0.10 |
| Trisodium citrate | 0.90 |
| Sodium benzoate | 0.25 |
| Sodium saccharine | 0.15 |
| Flavouring agent | 0.50 |

An unit dose of 5 ml of extemporaneous syrup was obtained containing 350 mg of active principle.

EXAMPLE 6

Granules intended or the reconstitution of an oral liquid preparation having the following composition, were prepared as described in Example 4:

|  | g |
|---|---|
| Compound of formula I | 8.00 |
| Saccharose | 45.60 |
| Sodium carboxymethylcellulose | 1.00 |
| Citric acid | 0.10 |
| Trisodium citrate | 0.90 |
| Sodium benzoate | 0.25 |
| Sodium saccharine | 0.15 |
| Flavouring agent | 0.50 |

An unit dose of 5 ml of extemporaneous syrup was obtained containing 400 mg of active principle.

EXAMPLE 7

Tablets having the following composition were prepared containing a compound described in Example 1:

|  | mg |
|---|---|
| Compound of formula I | 350 |
| Microcrystalline cellulose | 100 |
| Lactose | 125 |
| Magnesium stearate | 10 |
| Talc | 15 |
|  | 600 |

The powder was passed through a sieve with 0.3 mm mesh and the ingredients were mixed together until a homogeneous mixture was obtained which was compressed and granulated.

The granules thus obtained were compressed into tablets.

EXAMPLE 8

Tablets containing a compound described in Example 1 were prepared having the following composition:

|  | mg |
|---|---|
| Compound of formula I | 150 |
| Microcrystalline cellulose | 75 |
| Talc | 15 |
| Polyvinylpyrrolidone | 30 |
| Precipitated silica | 25 |
| Magnesium stearate | 5 |
|  | 300 |

All the ingredients with the exception of the lubricant, were thoroughly mixed in a mixing-kneading apparatus for 15 min. and the mixture obtained was kneaded with the gradual addition of water. The mass was passed through a sieve of 1.25 mm mesh and the granules were dried in an oven with forced ventilation until a relatively low degree of residual humidity (about 2%) was obtained. The granules were rendered uniform, the lubricant was added and the tablets were formed by compression.

Following the procedure described above, tablets containing 250 mg of active principle of formula I were prepared.

EXAMPLE 9

Coated tablets containing a compound described in Example 1 were prepared having the following composition and operating as described in Example 8:

|  | mg |
|---|---|
| Compound of formula I | 150 |
| Carboxymethylstarch | 10 |
| Microcrystalline cellulose | 85 |
| Lactose | 135 |
| Hydrogenated castor oil | 10 |
| Magnesium stearate | 5 |

The tablets thus obtained were covered with a coat having the following composition:

|  | mg |
| --- | --- |
| Butyl phthalate | 0.300 |
| Butyl and dimethylaminoethyl polymethacrylate | 1.850 |
| Polyethyleneglycol 1500 | 0.080 |
| Precipitated silica | 0.020 |
| Talc | 0.900 |
| Titanium dioxide | 1.850 |

This composition was dissolved in a solvent which was evaporated off in an oven with forced ventilation. Weigh of a tablet: 400 mg.

EXAMPLE 10

Suppositories having the following composition were prepared containing a compound described in Example 1:

|  | mg |
| --- | --- |
| Compound of formula I | 300 |
| Mass for suppositories | 1450 |
|  | 1750 |

The finely pulverized active substance was suspended in the mass for suppositories at 37° C. and the mixture was poured into moulds which were slightly cooled beforehand.

We claim:

1. A pharmaceutical or veterinary composition for treating drepanocytosis, malaria or babebiosis, which comprises an effective amount for inhibiting the malformation or destruction of red blood corpuscles due to genetic modification of the haemoglobin or to parasites of a thiosulfonate derivative having a formula:

$$R-S-SO_2-R_1$$

in which R represents a 1-methyl-imidazol-2-yl, 1H-benzimidazol-2-yl or benzoxazol-2-yl radical and $R_1$ represents a lower alkyl, (hydroxy)lower alkyl, lower alkanoyl, phenyl, (lower alkyl)phenyl, (hydroxy lower alkyl)phenyl, (lower alkanoyl)phenyl or quinolin-8-yl radical, in association with a pharmaceutical carrier or excipient therefor, and wherein said composition is in the form of a coated or uncoated tablet, a hard- or soft-gelatin capsule, a suspension or a syrup for oral administration, a suppository for rectal administration, a sterile solution or suspension for parenteral administration.

2. A composition according to claim 1, wherein the thiosulfonate derivative is benzoxazol-2-yl p-toluenethiosulfonate.

3. A composition according to claim 1, wherein each dosage unit contains from 10 to 1000 mg of active principle.

4. A composition according to claim 1 for treating drepanocytosis, malaria or babebiosis.

5. A composition according to claim 1, wherein the active principle is 1H-benzimidazol-2-yl benzenethiosulfonate.

6. A composition according to claim 1, wherein the active principle is 1H-benzimidazol-2-yl p-toluenethiosulfonate.

7. A composition according to claim 1, wherein the active principle is 1-methyl-H-imidazol-2-yl benzenethiosulfonate.

8. A composition according to claim 9, wherein the active principle is 1H-benzimidazol-2-yl methanethiosulfonate.

9. A method for treating drepanocytosis, malaria or babebiosis in a human host in need of such treatment comprising the administration to said host of an effective amount for treating drepanocytosis, malaria or babebiosis, of at least one thiosulfonate derivative having a formula:

$$R-S-SO_2-R_1$$

in which R represents a 1-methyl-imidazol-2-yl, 1H-benzimidazol-2-yl or benzoxazol-2-yl radical and $R_1$ represents a lowr alkyl, (hydroxy)lower alkyl, lowr alkanoyl, phenyl, (lower alkyl)phenyl, (hydroxy lower alkyl)phenyl, (lower alkanoyl)phenyl or quinolin-8-yl radical.

10. A method according to claim 9, wherein the thiosulfonate derivatives is benzoxazol-2-yl p-toluenethiosulfonate.

11. A method according to claim 9, wherein the effective dose is 0.1 to 100 mg/kg body-weight.

12. A method according to claim 10, wherein the effective dose is 0.1 to 100 mg/kg body-weight.

13. A method according to claim 9, wherein the active principle is 1H-benzimidazol-2-yl benzenethiosulfonate.

14. A method according to claim 9, wherein the active principle is 1H-benzimidazol-2-yl p-toluenethiosulfonate.

15. A method according to claim 9, wherein the active principle is 1-methyl-1H-imidazol-2-yl benzenethiosulfonate.

16. A method according to claim 9, wherrein the active principle is 1H-benzimidazole-2-yl methanethiosulfonate.

* * * * *